USOO5236843A

United States Patent [19]
Narva et al.

[11] Patent Number: 5,236,843
[45] Date of Patent: Aug. 17, 1993

[54] **GENE ENCODING A NEMATODE-ACTIVE TOXIN CLONED FROM A *BACILLUS THURINGIENSIS* ISOLATE**

[75] Inventors: Kenneth E. Narva, San Diego; George E. Schwab, La Jolla; Theresa Galasan; Jewel M. Payne, both of San Diego, all of Calif.

[73] Assignee: Mycogen Corporation, San Diego, Calif.

[21] Appl. No.: 669,126

[22] Filed: Mar. 14, 1991

Related U.S. Application Data

[63] Continuation-in-part of Ser. No. 565,544, Aug. 10, 1990, abandoned, which is a continuation-in-part of Ser. No. 84,653, Aug. 12, 1987, Pat. No. 4,948,734.

[51] Int. Cl.$^5$ .................. C12N 1/20; C12N 15/00; A01N 63/00
[52] U.S. Cl. ................ 435/252.3; 435/252.8; 435/320.1; 435/172.3; 530/350; 536/23.2; 424/93 A
[58] Field of Search ............... 435/252.3, 252.8, 320.1, 435/172.3; 530/350; 536/27, 23.2; 424/93

[56] References Cited

PUBLICATIONS

Prefontaine et al., *Appl. & Environ. Microb.*, Dec. 1987, vol. 53, No. 12, pp. 2808–2814.
Wabiko et al., *DNA*, vol. 5, No. 4, 1986, pp. 305–314.
Aronson et al., *Microbiological Reviews*, vol. 50, No. 1, Mar. 1986, pp. 1–24.
Honigman et al., *Gene*, vol. 42, 1986, pp. 69–77.
Prichard, R. K., C. A. Hall, J. D. Kelly, C. A. Martin, A. D. Donald (1980) "The Problem of Anthelmintic Resistance in Nematodes," Australian Veterinary Journal 56:239–251.
Coles, G. C. (1986) "Anthelmintic Resistance in Sheep", Veterinary Clinics of North America: Food Animal Practice 2(2): 423–432.
Bottjer, K. P., L. W. Bone, S. S. Gill (1985) "Nematoda: Susceptibility of the Egg to *Bacillus thuringiensis* Toxins," Invertebrate Parasitology 60: 239–244.
Ignoffo, C. M., V. H. Dropkin (1977) "Deleterious Effects of the Thermostable Toxin of *Bacillus thuringiensis* on Species of Soil-Inhabiting, Myceliophagous, and Plant-Parasitic Nematodes," J. Kansas Entomological Society 50(3): 394–398.
Ciordia, H., W. E. Bizzell (1961) "A Preliminary Report on the Effects of *Bacillus thuringiensis* var. *thuringiensis* Berliner on the Development of the Free-Living Stages of Some Cattle Nematodes," J. Parasitology 47:41 (abstract).

Primary Examiner—Robert A. Wax
Assistant Examiner—Keith D. Hendricks
Attorney, Agent, or Firm—Saliwanchik & Saliwanchik

[57] ABSTRACT

A novel B.t. gene encoding a toxin which is toxic to nematodes has been cloned from a *B. thuringiensis* microbe. The DNA encoding the B.t. toxin can be used to transform various prokaryotic and eukaryotic microbes to express the B.t. toxin. These recombinant microbes can be used to control nematodes in various environments.

7 Claims, 1 Drawing Sheet

GENE ENCODING A NEMATODE-ACTIVE TOXIN CLONED FROM A BACILLUS THURINGIENSIS ISOLATE

CROSS-REFERENCE TO A RELATED APPLICATION

This is a continuation-in-part of co-pending application Ser. No. 07/565,544, filed on Aug. 10, 1990 now abandoned, which is a continuation-in-part of application Ser. No. 07/084,653, filed on Aug. 12, 1987, now U.S. Pat. No. 4,948,734.

BACKGROUND OF THE INVENTION

Regular use of chemicals to control unwanted organisms can select for drug resistant strains. This has occurred in many species of economically important insects and has also occurred in nematodes of sheep, goats, and horses. The development of drug resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239-251; Coles, G. C. [1986] "Anthelmintic resistance in sheep," In *Veterinary Clinics of North America: Food Animal Practice*, Vol 2:423-432 [Herd, R. P., eds.] W. B. Saunders, New York). There are more than 100,000 described species of nematodes.

The bacterium *Bacillus thuringiensis* (B.t.) produces a δ-endotoxin polypeptide that has been shown to have activity against a rapidly growing number of insect species. The earlier observations of toxicity only against lepidopteran insects have been expanded with descriptions of B.t. isolates with toxicity to dipteran and coleopteran insects. These toxins are deposited as crystalline inclusions within the organism. Many strains of B.t. produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239-244, 1985) have reported that *B.t. kurstaki* and *B.t. israelensis* were toxic in vitro to eggs of the nematode *Trichostrongylus colubriformis*. In addition, 28 other B.t. strains were tested with widely variable toxicities. The most potent had $LD_{50}$ values in the nanogram range. Ignoffo and Dropkin (Ignoffo, C. M. and Dropkin, V. H. [1977] J. Kans. Entomol. Soc. 50:394-398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts. Advantageously, such effective means would employ biological agents. In grandparent application Ser. No. 07/084,653, there are disclosed novel isolates of *Bacillus thuringiensis* having activity against nematodes. In application Ser. No. 07/565,544, the applicants isolated, unexpectedly and advantageously, genes encoding novel nematicidal δ-endotoxins from the B.t. isolates PS33F2, PS63B, PS52A1, and PS69D1. Prior to successfully completing this invention, it could not be predicted with any reasonable degree of certainty that a gene(s) encoding a nematicidal toxin could be isolated because of the complexity of the microbial genome.

BRIEF SUMMARY OF THE INVENTION

The subject invention concerns a gene cloned from a *Bacillus thuringiensis* isolate designated B.t. PS52A1. The gene of the invention encodes an approximately 55-60 kDa δ-endotoxin protein, as determined by SDS-PAGE analysis, which has nematicidal activity. The gene can be transferred to suitable hosts via a recombinant DNA vector.

DETAILED DISCLOSURE OF THE INVENTION

Figure 1:
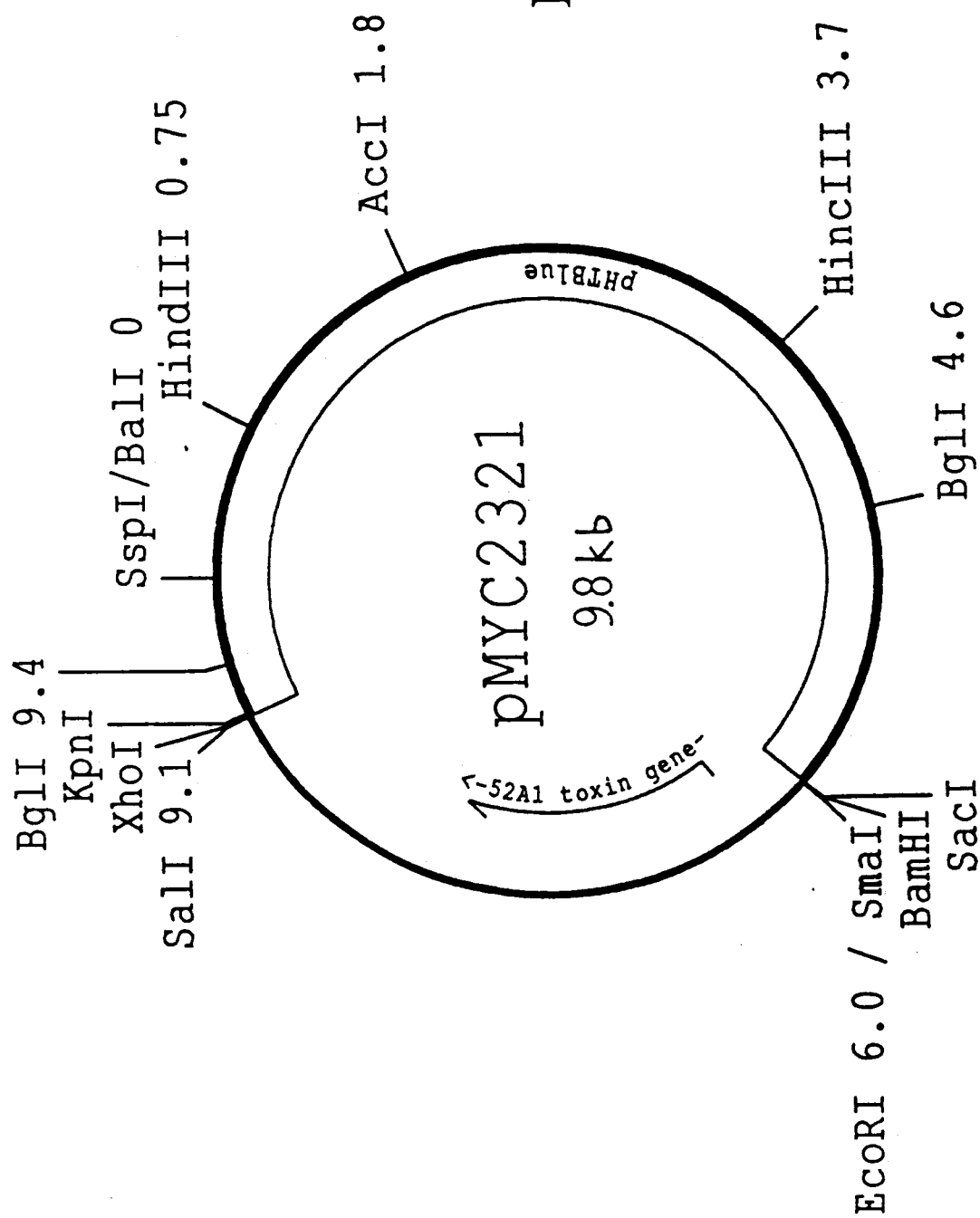
FIG. 1 is a restriction map of plasmid pMYC2321.

The novel toxin gene of the subject invention was obtained from the nematode-active *Bacillus thuringiensis* (B.t.) isolate designated PS52A1. A subculture of the *E. coli* host harboring the toxin gene of the invention was deposited in the permanent collection of the Northern Research Laboratory, U.S. Department of Agriculture, Peoria, Ill., USA. The accession numbers are as follows:

| Culture | Repository No. | Deposit Date |
| --- | --- | --- |
| B.t. isolate PS52A1 | NRRL B-18245 | July 28, 1987 |
| E. coli NM522(pMYC2321) | NRRL B-18770 | February 14, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The novel B.t. gene or gene fragments of the invention encode a toxin which shows activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The toxin encoded by the novel B.t. gene of the invention is useful as a nematicide for the control of soil nematodes and plant parasites selected from the genera Bursaphalenchus, Criconemella, Ditylenchus, Globodera, Helicotylenchus, Heterodera, Melodiogyne, Pratylenchus, Radopholus, Rotelynchus, or Tylenchus.

Alternatively, because some plant parasitic nematodes are obligate parasites, genes coding for nematocidal B.t. toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387–399, 1984).

The B.t. toxin of the invention can be administered orally in a unit dosage form such as a capsule, bolus or tablet, or as a liquid drench when used as an anthelmintic in mammals. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compound in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraluminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxin is administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

The toxin gene or gene fragments of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they will proliferate and be ingested by the nematodes. The result is a control of the nematodes. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototrophy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Where the B.t. toxin gene or gene fragment is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are known and available for introducing the B.t. gene or gene fragments expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene or gene fragment into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for inges-tion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp., phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the B.t. toxin gene or gene fragment, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. nematicidal gene or gene fragment may be grown in any convenient nutrient medium, where the DNA construct provides a selective advantage, providing for a selective medium so that substantially all or all of the cells retain the B.t. gene or gene fragment. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration will vary widely depending upon the nature of the particular formulation, particularly whether it is a concentrate or to be used directly. The nematicide will be present in at least 1% by weight and may be 100% by weight. The dry formulations will have from about 1-95% by weight of the nematicide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolate of the Invention

A subculture of B.t. isolate B.t. PS52A1 can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |

The salts solution and CaCl$_2$ solution are filter-sterilized and added to the autoclaved and cooked broth at the time of inoculation. Flasks are incubated at 30° C. on a rotary shaker at 200 rpm for 64 hr.

EXAMPLE 2

Purification of Protein and Amino Acid Sequencing

The B.t. isolate PS52A1 was cultured as described in Example 1. The parasporal inclusion bodies were partially purified by sodium bromide (23-38%) isopycnic gradient centrifugation (Pfannenstiel, M. A., E. J. Ross, V. C. Kramer, and K. W. Nickerson [1984] FEMS Microbiol. Lett. 21:39). The protein toxic for the nematode Caenorhabditis elegans was bound to PVDF membranes (Millipore, Bedford, Mass.) by western blotting techniques (Towbin, H., T. Staehlelin, and K. Gordon [1979] Proc. Natl. Acad. Sci. USA 76:4350) and the N-terminal amino acid sequence was determined by the standard Edman reaction with an automated gas-phase sequenator (Hunkapiller, M. W., R. M. Hewick, W. L. Dreyer, and L. E. Hood [1983] Meth. Enzymol. 91:399). The sequence obtained was:

PS52A1 MIIDSKTTLPRHSLINT

From this sequence data an oligonucleotide probe was designed by utilizing a codon frequency table assembled from available sequence data of other B.t. toxin genes. The probe was synthesized on an Applied Biosystems, Inc. DNA synthesis machine.

Protein purification and subsequent amino acid analysis of the N-terminal peptide listed above has led to the deduction of several oligonucleotide probes for the isolation of toxin genes from nematicidal B.t. isolates. RFLP analysis of restricted total cellular DNA using radiolabeled oligonucleotide probes has elucidated a different gene or gene fragments. The following table reviews the data.

TABLE 1

| Size (kb) restriction fragment hybridizing with probe C under HindIII restriction | |
|---|---|
| B.t. Isolate | Probe C |
| PS52A1 | 3.6 |

Probe C has the following sequence:
5'-ATG ATT ATT GAT TCT AAA ACA ACA TTA CCA AGA CAT TCT/A TTA ATT/A AAT ACA/T ATT/A AA-3'

EXAMPLE 3

Molecular Cloning of Gene Encoding a Novel Toxin from *Bacillus thuringiensis* Strain PS52A1

Total cellular DNA was prepared from *Bacillus thuringiensis* PS52A1 cells grown to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE and RNase was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Restriction fragment length polymorphism (RFLP) analyses were performed by standard hybridization of Southern blots of B.t. PS52A1 DNA with a $^{32}$P-labeled oligonucleotide probe, Probe C above. Hybridizing bands included an approximately 3.6 kbp HindIII fragment and an approximately 8.6 kbp EcoRV fragment.

A gene library was constructed from B.t. PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega). Recombinant phage were packaged and plated on *E. coli* KW251 cells (Promega). Plaques were screened by hybridization with the radiolabeled Probe C. Hybridizing phage were plaque-purified and used to infect liquid cultures of *E. coli* KW251 cells for isolation of phage DNA by standard procedures (Maniatis et al.). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI+SalI-digested pHTBlueII (an *E. coli/B. thuringiensis* shuttle vector comprised of pBluescript S/K [Stratagene] and the replication origin from a resident B.t. plasmid [D. Lereclus et al. (1989) FEMS Microbiology Letters 60:211–218]). The ligation mix was used to transform frozen, competent *E. coli* NM522 (ATCC 47000). Transformants were plated on LB agar containing ampicillin, isopropyl-($\beta$)-D-thiogalactoside (IPTG), and 5-bromo-chloro-3-indolyl-($\beta$)-D-galactoside (XGAL). Plasmids were purified from putative recombinants by alkaline lysis (Maniatis et al.) and analyzed by electrophoresis of EcoRI and SalI digests on agarose gels. The desired plasmid construct, pMYC2321, contains a toxin gene that is novel compared to the maps of other toxin genes encoding nematicidal proteins.

Plasmid pMYC2321 was introduced into an acrystalliferous (Cry−) B.t. host (B.t. HD-1 Cry B, A. I. Aronson, Purdue University, West Lafayette, Ind.) by electroporation. Expression of an approximately 55–60 kDa crystal protein was verified by SDS-PAGE analysis and nematicidal activity. NaBr-purified crystals were prepared (Pfannenstiel, M. A., et al., supra) for determination of toxicity of the cloned gene product to *Pratylenchus scribneri* (Plant-Parasitic) and *Panagrellus redivivus* (Free-Living). The cloned gene product was active against these nematodes.

EXAMPLE 4

Insertion of Toxin Gene Into Plants

The novel gene coding for the novel nematode-active toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J. [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 5

Cloning of Novel *Bacillus thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

We claim:

1. An isolated DNA molecule encoding an ≈55–60 kDa *Bacillus thuringiensis* PS52A1 toxin active against nematodes.

2. A recombinant DNA transfer vector comprising DNA encoding an ≈55–60 kDa *Bacillus thuringiensis* PS52A1 toxin active against nematodes.

3. A prokaryotic or eukaryotic microorganism or plant cell host, transformed by the transfer vector of claim 2.

4. A microorganism transformed by the vector of claim 2 to express an ≈55–60 kDa *Bacillus thuringiensis* PS52A1 toxin active against nematodes.

5. A microorganism according to claim 4, wherein said microorganism is *Escherichia coli* NM522(pMYC2321), having an accession number NRRL B-18770.

6. The microorganism, according to claim 4, which is a species of Pseudomonas, Bacillus, Azotobacter, Erwinia, Serratia, Klebsiella, Rhizobium, Rhodopseudomonas, Methylophilius, Agrobacterium, Acetobacter or Alcaligenes.

7. Plasmid denoted pMYC2321.

* * * * *

UNITED STATES PATENT AND TRADEMARK OFFICE
CERTIFICATE OF CORRECTION

PATENT NO.   :   5,236,843

DATED        :   August 17, 1993

INVENTOR(S)  :   Kenneth E. Narva, George E. Schwab, Theresa Galasan and Jewel Payne It is certified that error appears in the above-identified patent and that said Letters Patent is hereby corrected as shown below:

Column 9    line 45:  After "$FeSO_4 \cdot 7H_2O$      0.40 g" add the following:

--$CaCl_2$ Solution (100 ml)
   $CaCl_2 \cdot 2H_2O$      3.66 g
pH 7.2--

Column 9    line 55:  Delete "(23-38%)" and insert --(28-38%)--.

Signed and Sealed this

Eighth Day of March, 1994

Attest:

BRUCE LEHMAN

Attesting Officer

Commissioner of Patents and Trademarks